United States Patent
Lin et al.

(10) Patent No.: US 9,944,673 B2
(45) Date of Patent: Apr. 17, 2018

(54) CRYSTALLINE FORMS OF 5α-ANDROSTANE-3β,5,6β-TRIOL AND PREPARATION METHODS THEREFOR

(71) Applicant: GUANGZHOU CELLPROTEK PHARMACEUTICAL CO., LTD., Guangzhou (CN)

(72) Inventors: Suizhen Lin, Guangzhou (CN); Jingxia Zhang, Guangzhou (CN); Xinhua Li, Guangzhou (CN)

(73) Assignee: GUANGZHOU CELLPROTEK PHARMACEUTICAL CO., LTD., Guangzhou (CN)

( * ) Notice: Subject to any disclaimer, the term of this patent is extended or adjusted under 35 U.S.C. 154(b) by 0 days.

(21) Appl. No.: 15/589,268

(22) Filed: May 8, 2017

(65) Prior Publication Data

US 2017/0305958 A1 Oct. 26, 2017

Related U.S. Application Data (62) Division of application No. 14/383,405, filed as application No. PCT/CN2012/073854 on Apr. 11, 2012, now Pat. No. 9,688,716.

(30) Foreign Application Priority Data

Mar. 8, 2012 (CN) .......................... 2012 1 0060611

(51) Int. Cl.
*C07J 1/00* (2006.01)

(52) U.S. Cl.
CPC ......... *C07J 1/0007* (2013.01); *C07B 2200/13* (2013.01)

(58) Field of Classification Search
CPC .......................... C07J 1/0007; C07B 2200/13
See application file for complete search history.

(56) References Cited

U.S. PATENT DOCUMENTS

| | | | |
|---|---|---|---|
| 2,191,576 A | 2/1940 | Miescher et al. | |
| 8,809,309 B2 | 8/2014 | Yan et al. | |
| 2013/0172307 A1 | 7/2013 | Yan et al. | |

FOREIGN PATENT DOCUMENTS

| | | |
|---|---|---|
| CN | 101884638 A | 11/2010 |
| CN | 101961311 A | 2/2011 |
| EP | 2 591 785 A1 | 5/2013 |
| WO | WO 2012/003802 A1 | 1/2012 |

OTHER PUBLICATIONS

Ohuchi et al, Chemical & Pharmaceutical Bulletin, The Reaction of Lead Tetraacetate with 3-beta-Hydroxy Steroids, 1981, 29(1), pp. 43-50.*
Wikipedia, Wikipedia, Tilde, recovered from https://en.wikipedia.org/wiki/Tilde on Mar. 23, 2017, pp. 1-19.*
International Search Report dated Dec. 27, 2012, for International Application No. PCT/CN2012/073854, (2 pages).
Ohuchi et al., Chemical & Pharmaceutical Bulletin, The Reaction of Lead Tetraacetate with 3.BETA.-Hydroxy Steroids, 1981, 29(1), pp. 43-50.
Armarego et al., Purification of Laboratory Chemicals, 2000 Buttenworth-Heinemann, Woburn, MA, pp. 1-47.
Supplementary European Search Report, dated Aug. 26, 2015, for European Application No. EP 12 87 0566, 9 pgs.
Baldwin et al., "The Base-catalysed Epoxidation of Androst-4-en-6-ones", Journal of the Chemical Society, Perkin Transactions 1, vol. 16, Jan. 1, 1972. pp. 2051-2054.
Fetizon et al., "Oxydations Par Le Carbonate D'Argent Sur Celite-X", Tetrahedron, vol. 30, Jan. 1, 1974, pp. 327-335.
Sciaky et al., "Syntheses of 4-androstene-3,6-dione and 4-pregnene-3,6-dione", Gazzetta Chimica Italiana, 92, 1962, pp. 730-737.
Weinman et al., Steroids, vol. 6, No. 6, 1965, pp. 699-705.

* cited by examiner

*Primary Examiner* — Paul A Zucker
(74) *Attorney, Agent, or Firm* — Finnegan, Henderson, Farabow, Garrett & Dunner LLP (57) ABSTRACT

The present invention relates to four crystalline forms (crystalline forms A, B, C and D) of 5α-androstane-3β,5,6β-triol (YC-6) and preparation methods therefor. The four crystalline forms have significant difference in their lattice parameters, 2θ values and intensity in X-ray power diffraction, and melting points, etc. The study on its polymorphism is very important for further studying its effect, bioavailability and stability.

4 Claims, 12 Drawing Sheets

CRYSTALLINE FORMS OF 5α-ANDROSTANE-3β,5,6β-TRIOL AND PREPARATION METHODS THEREFOR

CROSS-REFERENCE TO RELATED APPLICATIONS

This application is a divisional application of and claims the benefit of priority to U.S. application Ser. No. 14/383,405, filed Sep. 5, 2014, now U.S. Pat. No. 9,688,716, which is a National Stage Entry of International Application No. PCT/CN2012/073854, filed Apr. 11, 2012, which claims priority to Chinese Application No. 201210060611.6, filed Mar. 8, 2012. The contents of the above-referenced applications are incorporated herein by reference in their entireties.

FIELD OF THE INVENTION

The present invention relates to crystalline forms of 5α-androstane-3β,5,6β-triol (also known as 5α-androst-3β,5,6β-triol). The present invention also relates to preparation methods for the crystalline forms of 5α-androstane-3β,5,6β-triol.

BACKGROUND OF THE INVENTION

Polymorphism is common in solid drugs, and drug compounds in different crystalline forms have different physical and chemical properties. Polymorphism is one of important factors that have influence on the effect and quality of solid drugs. Different crystalline forms may differ by several times in solubility, and also differ greatly in in vivo distribution and metabolism, causing differences in bioavailability. In addition, solid APIs (active pharmaceutical ingredients) in different crystalline forms and preparations thereof show different stabilities during preparation and storage process, which would cause crystalline transformation and thus influence the quality of the drugs. Therefore, the polymorphism would finally influence the quality, therapeutic effect and safety of solid drugs.

5α-androstane-3β,5,6β-triol is one of polyhydroxy steroids, and has significant neuroprotective effect. The study on its polymorphism is very important for further studying its efficacy, bioavailability and stability. X-ray single crystal diffractometer, X-ray powder diffractometer and differential thermal analyzer are main tools for quantitatively determining the specific type of polymorphism, which provides more qualitative and quantitative information for the study on crystalline form of solid drugs.

SUMMARY OF THE INVENTION

An object of the present invention is to provide four crystalline forms of 5α-androstane-3β,5,6β-triol (hereinafter abbreviated as YC-6).

Another object of the present invention is to provide methods for preparing the four crystalline forms of 5α-androstane-3β,5,6β-triol.

A first crystalline form of 5α-androstane-3β,5,6β-triol (hereinafter abbreviated as crystalline form A of YC-6) is provided by the present invention, wherein the crystalline form is a transparent block-shaped crystal, and belongs to the monoclinic crystal system and space group $P2_1$, and wherein the crystalline form is characterized by lattice parameters of a=17.8±0.2 Å, b=7.3±0.2 Å, c=22.1±0.2 Å, α=90.0°, β=103.3±0.5°, γ=90.0°; and characterized by diffraction peaks at diffraction angle 2θ values of 4.4±0.2, 8.7±0.2, 9.3±0.2, 12.6±0.2, 13.0±0.2, 15.0±0.2, 15.6±0.2, 16.6±0.2, 17.3±0.2, 18.5±0.2, 19.6±0.2, 21.0±0.2, 21.8±0.2, 24.3±0.2, 27.9±0.2 degrees; and characterized by the endothermic transition temperature of 225±2° C.

A method for preparing the crystalline form A of YC-6 is provided by the present invention, comprising: dissolving 5α-androstane-3β,5,6β-triol in a solvent at room temperature or at 50-80° C., with a ratio of the 5α-androstane-3β,5,6β-triol to the solvent being 1 g:10-40 mL; adding another solvent to dilute; allowing to form a crystalline precipitate.

Preferably, in the above method, the solvent for dissolving is acetone, methanol, ethanol, isopropanol, dioxane or tetrahydrofuran, and the solvent for diluting is an original solvent or a poor solvent, wherein the original solvent is acetone, methanol, ethanol, isopropanol or dioxane (excluding tetrahydrofuran) with a dilution rate of 0-5:1, and the poor solvent is water with a dilution rate of 0-2:1.

A second crystalline form of 5α-androstane-3β,5,6β-triol (hereinafter abbreviated as crystalline form B of YC-6) is provided by the present invention, wherein the crystalline form is a transparent needle-shaped crystal, and belongs to the monoclinic crystal system and space group $P2_1$, and wherein the crystalline form is characterized by lattice parameters of a=11.3±0.2 Å, b=7.4±0.2 Å, c=20.5±0.2 Å, α=90.0°, β=95.0±0.5°, γ=90.0°; and characterized by diffraction peaks at diffraction angle 2θ values of 4.3±0.2, 8.6±0.2, 12.9±0.2, 17.2±0.2, 21.6±0.2 degrees; and characterized by the endothermic transition temperature of 223±2° C.

A method for preparing the crystalline form B of YC-6 is provided by the present invention, comprising: dissolving 5α-androstane-3β,5,6β-triol in a solvent, with a ratio of the 5α-androstane-3β,5,6β-triol to the solvent being 1 g:10-120 mL; heating to 50-80° C.; adding another solvent to dilute; cooling; allowing to form a crystalline precipitate.

Preferably, in the above method, the solvent for dissolving is acetone, ethyl acetate or ethanol, and the solvent for diluting is an original solvent or a poor solvent, wherein the original solvent is acetone, ethyl acetate or ethanol, and the poor solvent is water, hexamethylene or petroleum ether.

More preferably, in the above method, the dilution rate is 2.5-5:1 when acetone or ethanol is used as the solvent for dissolving and water is used as the poor solvent for diluting; the dilution rate is 1-5:1 when acetone or ethanol is used as the solvent for dissolving and hexamethylene or petroleum ether is used as the poor solvent for diluting; the dilution rate is 0-5:1 when ethyl acetate is used as the solvent for dissolving and ethyl acetate is used as the original solvent for diluting; and the dilution rate is 0-5:1 when ethyl acetate is used as the solvent for dissolving and hexamethylene or petroleum ether is used as the poor solvent for diluting.

A third crystalline form of 5α-androstane-3β,5,6β-triol (hereinafter abbreviated as crystalline form C of YC-6) is provided by the present invention, wherein the crystalline form is a transparent plate-shaped crystal, and belongs to the monoclinic crystal system and space group $P2_1$, and wherein the crystalline form is characterized by lattice parameters of a=17.1±0.2 Å, b=6.4±0.2 Å, c=34.9±0.2 Å, α=90.0°, β=91.1±0.5°, γ=90.0°; and characterized by diffraction peaks at diffraction angle 2θ values of 4.2±0.2, 8.5±0.2, 9.0±0.2, 12.5±0.2, 14.8±0.2, 15.4±0.2, 16.4±0.2, 16.8±0.2, 17.1±0.2, 18.3±0.2, 19.4±0.2, 20.8±0.2, 21.8±0.2, 24.1±0.2 degrees; and characterized by the endothermic transition temperature of 206±2° C.

A method for preparing the crystalline form C of YC-6 is provided by the present invention, comprising: dissolving 5α-androstane-3β,5,6β-triol in ethanol at room temperature, with a ratio of the 5α-androstane-3β,5,6β-triol to the ethanol being 1 g:10-30 mL; adding ethanol in a ratio of 0-5:1 to dilute; allowing to form a crystalline precipitate at 0-10° C.

A fourth crystalline form of 5α-androstane-3β,5,6β-triol (hereinafter abbreviated as crystalline form D of YC-6) is provided by the present invention, wherein the crystalline form is a transparent column-shaped crystal, and belongs to the orthorhombic crystal system and space group $P2_12_12_1$, and wherein the crystalline form is characterized by lattice parameters of a=6.3±0.2 Å, b=12.6±0.2 Å, c=26.7±0.2 Å, α=90.0°, β=90°, γ=90.0°; and characterized by diffraction peaks at diffraction angle 2θ values of 4.0±0.2, 8.1±0.2, 8.5±0.2, 9.4±0.2, 12.5±0.2, 14.0±0.2, 14.9±0.2, 15.5±0.2, 16.4±0.2, 17.1±0.2, 18.3±0.2, 19.5±0.2, 20.5±0.2, 20.9±0.2, 21.5±0.2 degrees; and characterized by the endothermic transition temperature of 226±2° C.

A method for preparing the crystalline form D of YC-6 is provided by the present invention, comprising: dissolving 5α-androstane-3β,5,6β-triol in tetrahydrofuran at room temperature, with a ratio of the 5α-androstane-3β,5,6β-triol to the tetrahydrofuran being 1 g:10-30 mL; adding tetrahydrofuran in a ratio of 0-5:1 to dilute; allowing to form a crystalline precipitate.

The four crystalline forms of 5α-androstane-3β,5,6β-triol (i.e., crystalline forms A, B, C and D of YC-6) provided by the present invention have significant differences in their lattice parameters, 2θ values and intensity in X-ray power diffraction, and melting points, etc. The study on its polymorphism is significant for further studying of its efficacy, bioavailability and stability.

DETAILED DESCRIPTION OF THE INVENTION

Physical Characterization

X-ray single crystal diffraction diagrams for different crystalline forms of YC-6, which were obtained by the examples, were obtained using Xcalibur Nova biomacromolecule X-Ray single crystal diffractometer (Agilent Technologies (China) Co., Ltd), under the following settings: fixed target of copper; output power: 50 W; two-dimensional surface detecting system: 165 mmCCD; resolution: ≤0.005 degree; cooling nitrogen: −180+approx. 25° C.; control accuracy: ≤0.5° C.; test temperature: 150 k.

X-ray powder diffraction diagrams for different crystalline forms of YC-6, which were obtained by the examples, were obtained using D/Max-IIIA X-ray powder diffractometer (Rigaku, Japan), under the following settings: fixed target of copper; power: 3 kW; detecting angle: 1-50°; sensitivity: 3-5%; accuracy of the detecting angle: ±0.002.

Differential scanning for different crystalline forms of YC-6, which were obtained by the examples, were performed using STA409PC thermal analyzer (Netzsch, Germany), under the following settings: crucible: alumina crucible; carrier gas: $N_2$; temperature: 20-400° C., 10.0 K/min, 400° C. maintained by 10 min.

Analysis Parameters of the Single Crystal Diffraction, Powder Diffraction and DSC for the Four Crystalline Forms of YC-6

Figure 1:
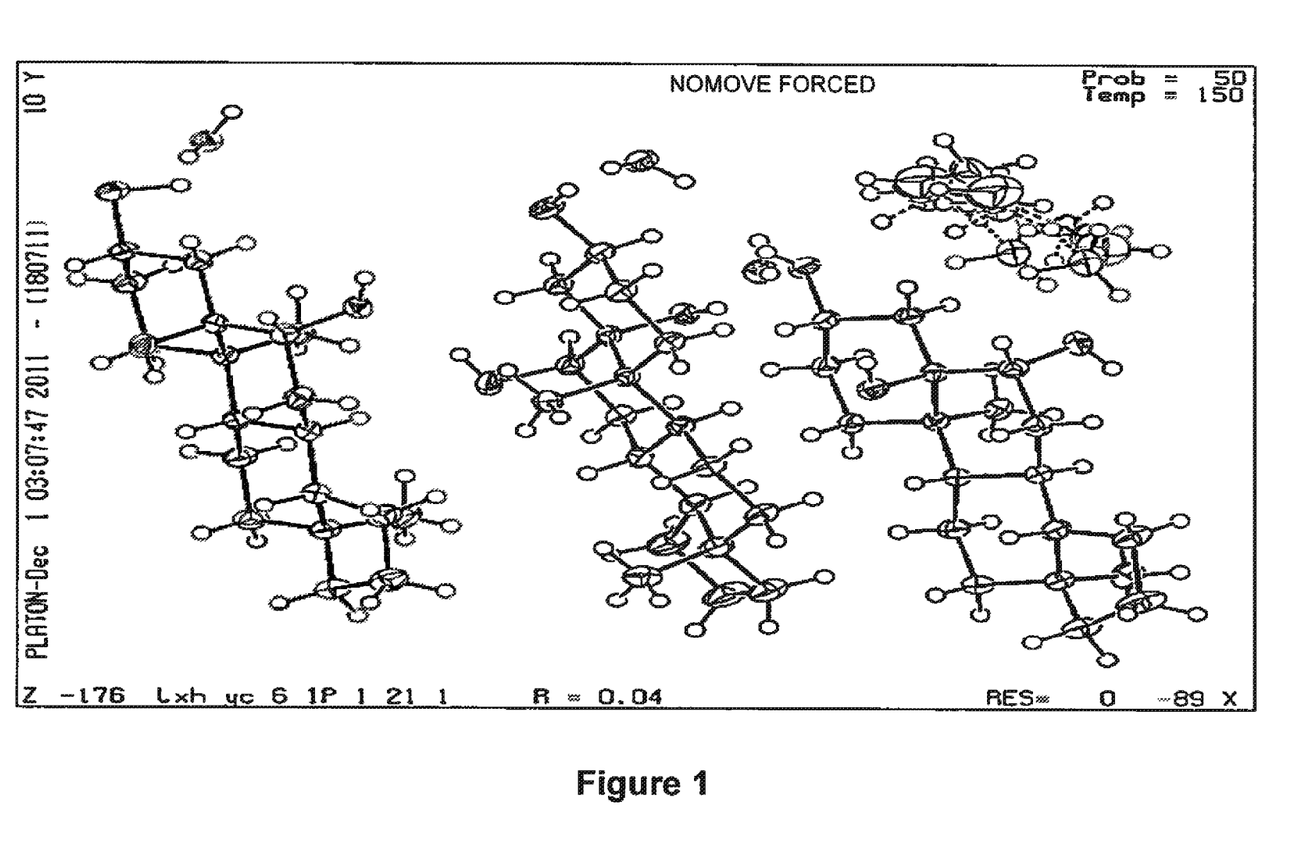
FIG. 1 shows the X-ray single crystal diffraction diagrams of crystalline form A of YC-6.

(1) The crystal structure information of crystalline form A of YC-6 obtained by X-ray single crystal diffraction is: the crystalline form belongs to the monoclinic crystal system and space group $P2_1$, with lattice parameters of a=17.76±0.08 Å, b=7.30±0.08 Å, c=22.05±0.08 Å, α=90.0°, β=103.23±0.5°, γ=90.0°, V=2775.36(5) Å³.

Figure 2:
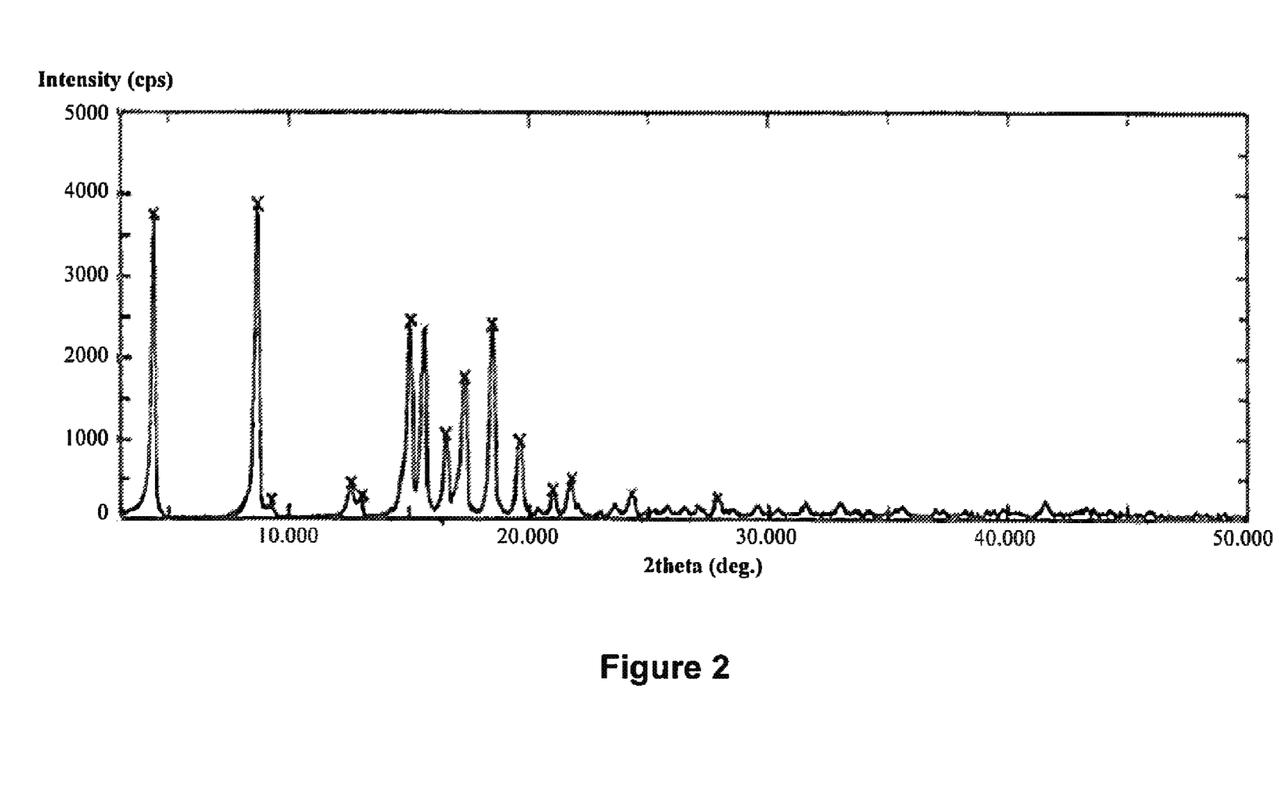
FIG. 2 shows the X-ray powder diffraction diagrams of crystalline form A of YC-6.

The crystalline form A of YC-6 showed diffraction peaks at diffraction angle 2θ values of 4.4±0.1, 8.7±0.1, 9.3±0.1, 12.6±0.1, 13.0±0.1, 15.0±0.1, 15.6±0.1, 16.6±0.1, 17.3±0.1, 18.5±0.1, 19.6±0.1, 21.0±0.1, 21.8±0.1, 24.3±0.1, 27.9±0.1 degrees, with the X-ray powder diffraction diagrams showed in FIG. 2.

Figure 3:
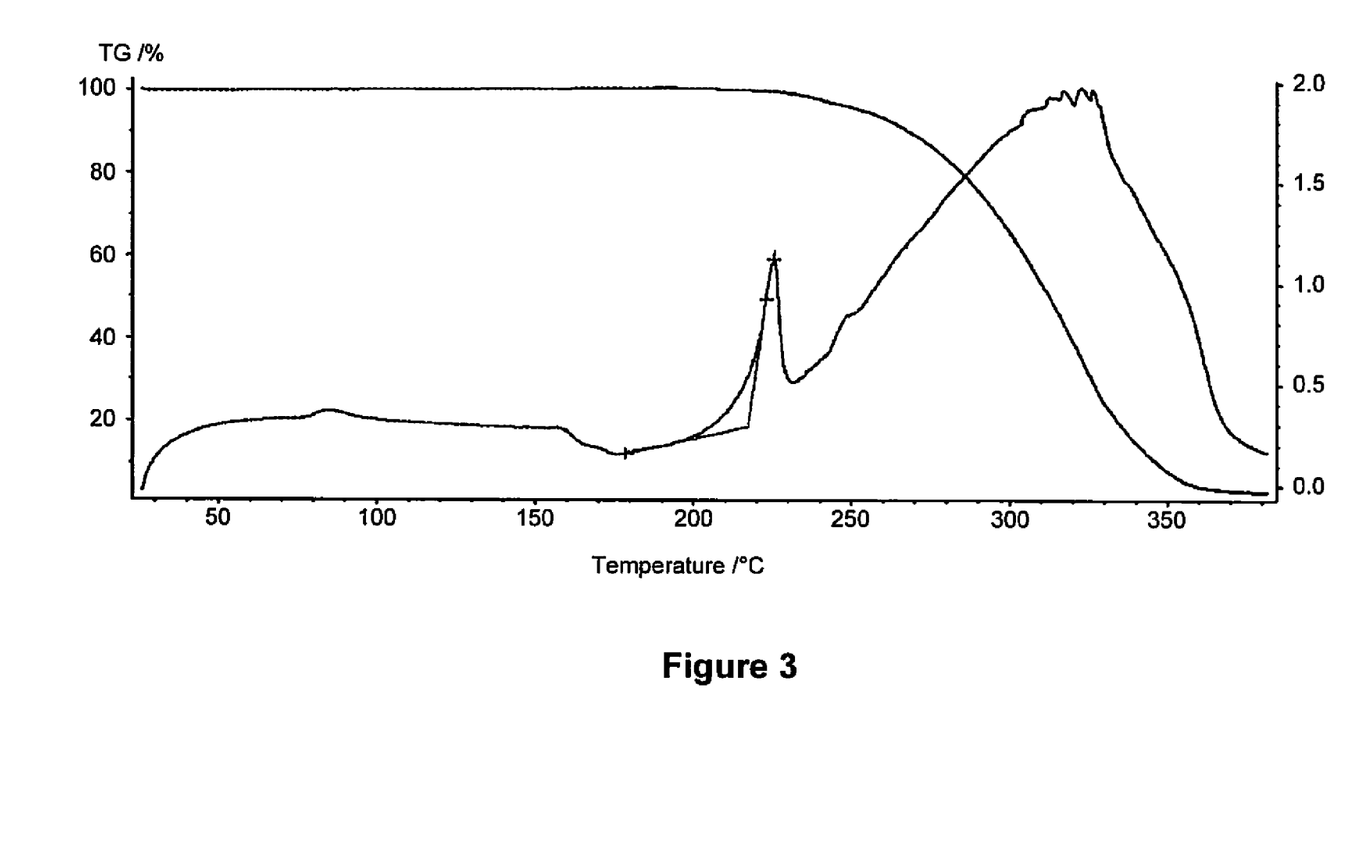
FIG. 3 shows the differential thermal analysis diagrams of crystalline form A of YC-6.

The differential scanning calorimetry (DSC) diagrams of crystalline form A of YC-6 is showed in FIG. 3, with the endothermic transition temperature of 225±2° C.

Figure 4:
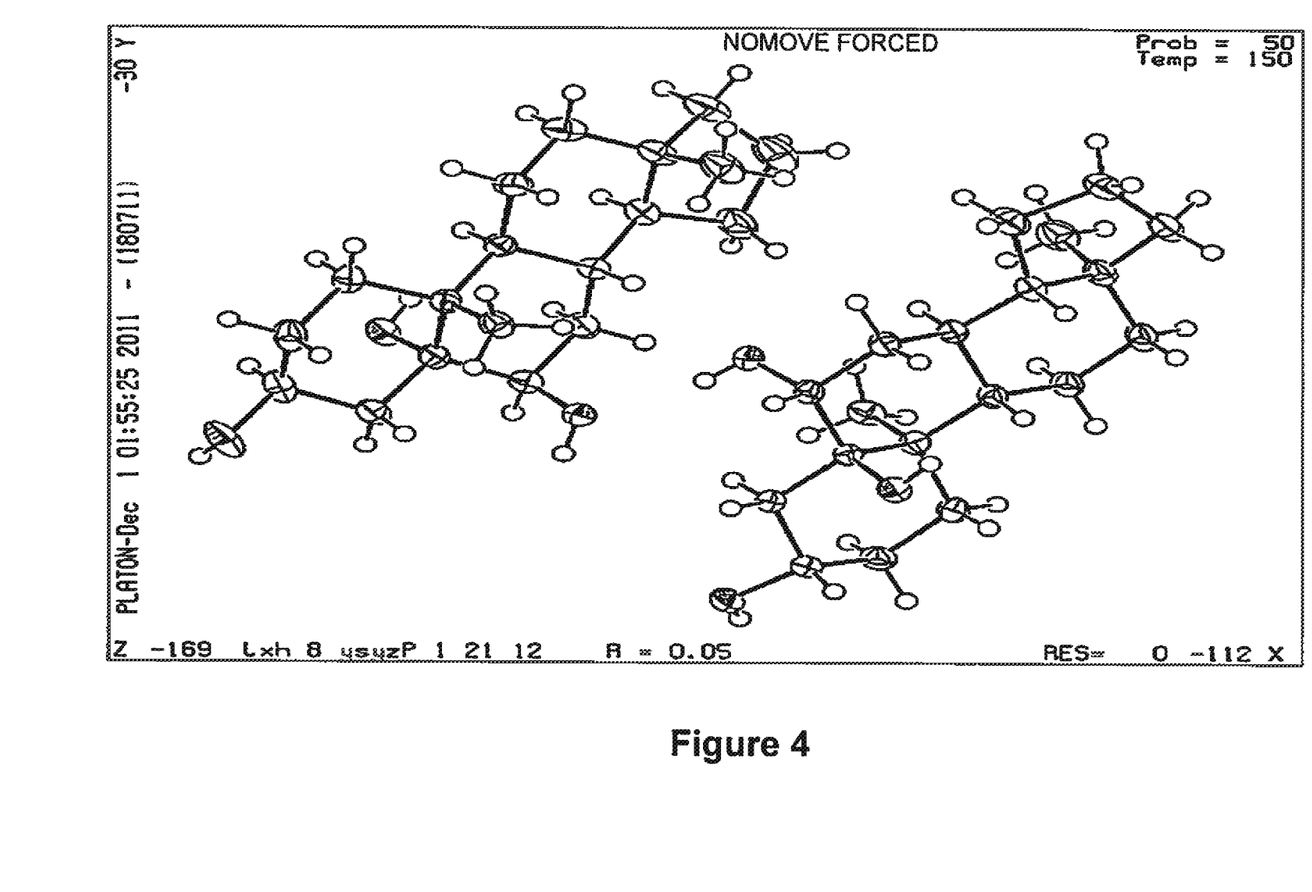
FIG. 4 shows the X-ray single crystal diffraction diagrams of crystalline form B of YC-6.

(2) The crystal structure information of crystalline form B of YC-6 obtained by X-ray single crystal diffraction is: the crystalline form belongs to the monoclinic crystal system and space group $P2_1$, with lattice parameters of a=11.27±0.08 Å, b=7.40±0.08 Å, c=20.45±0.08 Å, α=90.0°, β=94.94±0.5°, γ=90.0°, V=1699.24(3) Å³.

Figure 5:
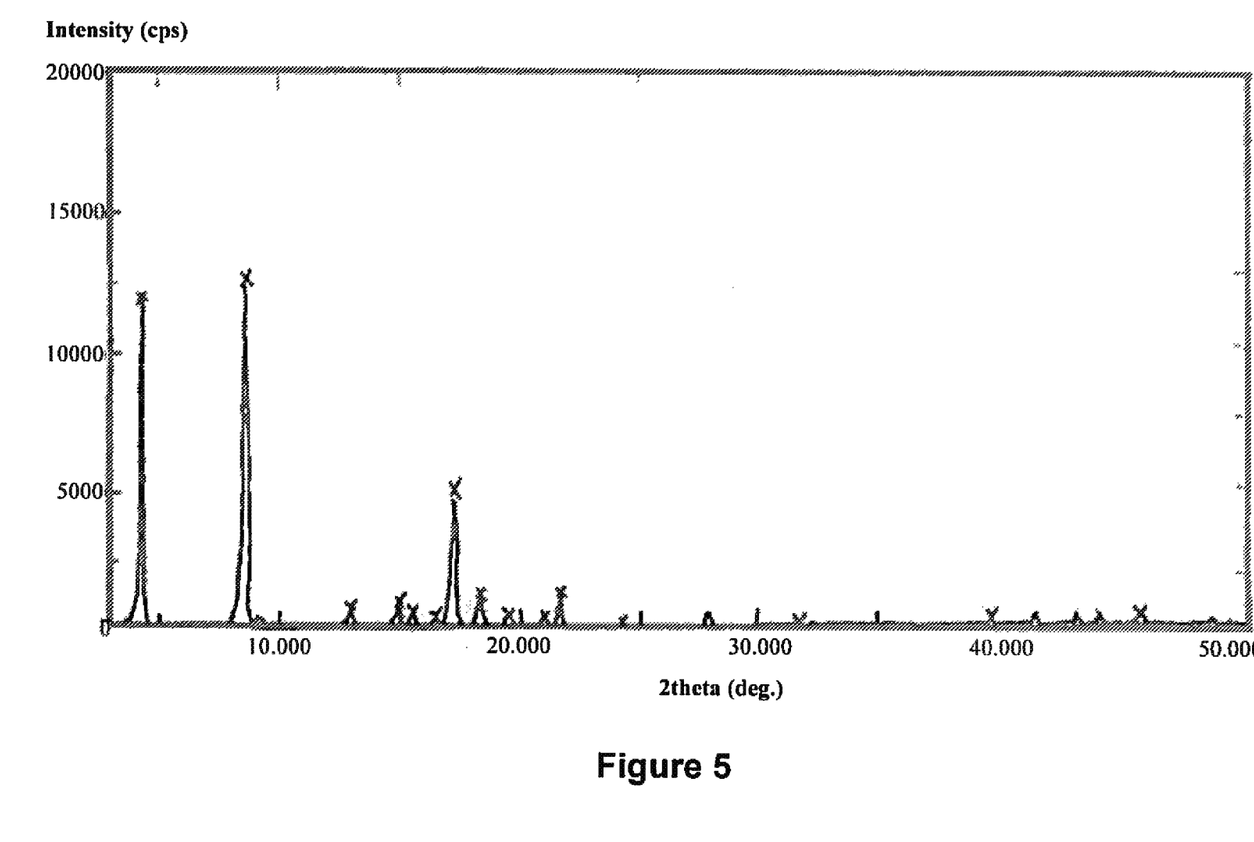
FIG. 5 shows the X-ray powder diffraction diagrams of crystalline form B of YC-6.

The crystalline form B of YC-6 showed diffraction peaks at diffraction angle 2θ values of 4.3±0.1, 8.6±0.1, 12.9±0.1, 17.2±0.1, 21.6±0.1 degrees, with the X-ray powder diffraction diagrams showed in FIG. 5.

Figure 6:
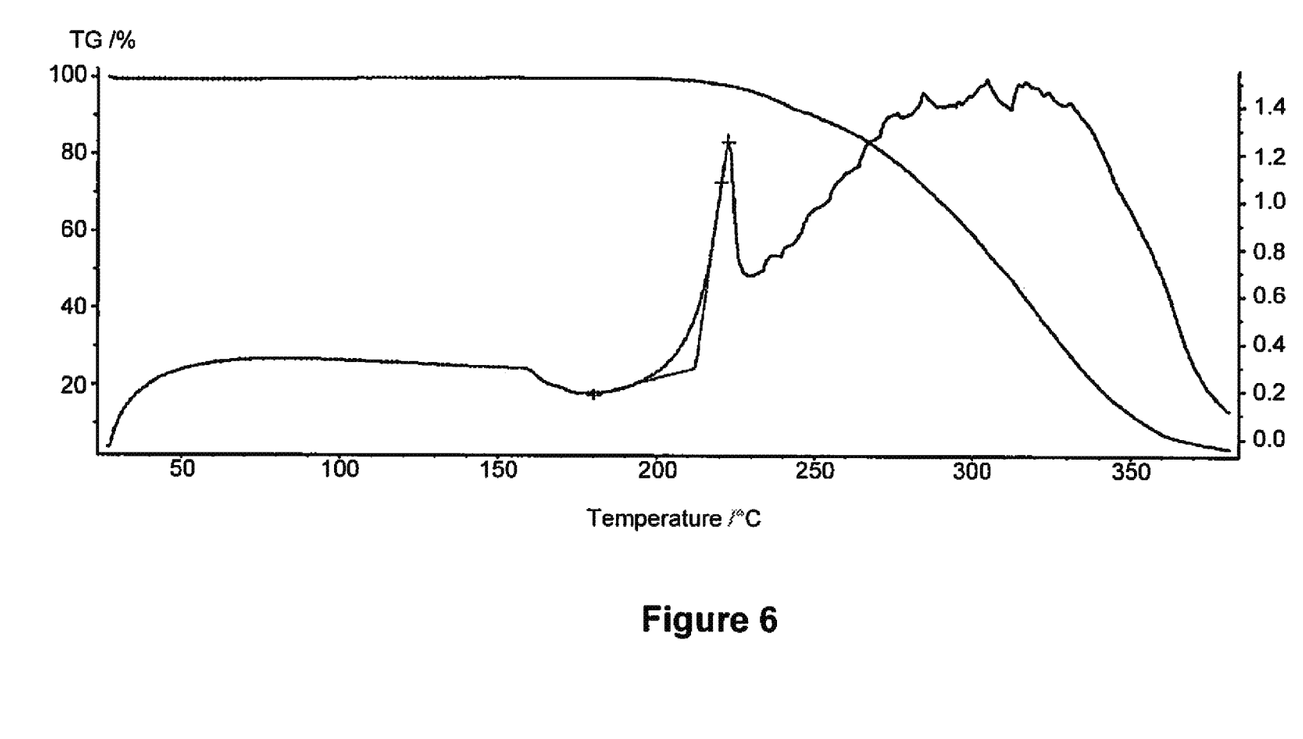
FIG. 6 shows the differential thermal analysis diagrams of crystalline form B of YC-6.

The differential scanning calorimetry (DSC) diagrams of crystalline form B of YC-6 is showed in FIG. 6, with the endothermic transition temperature of 223±2° C.

Figure 7:
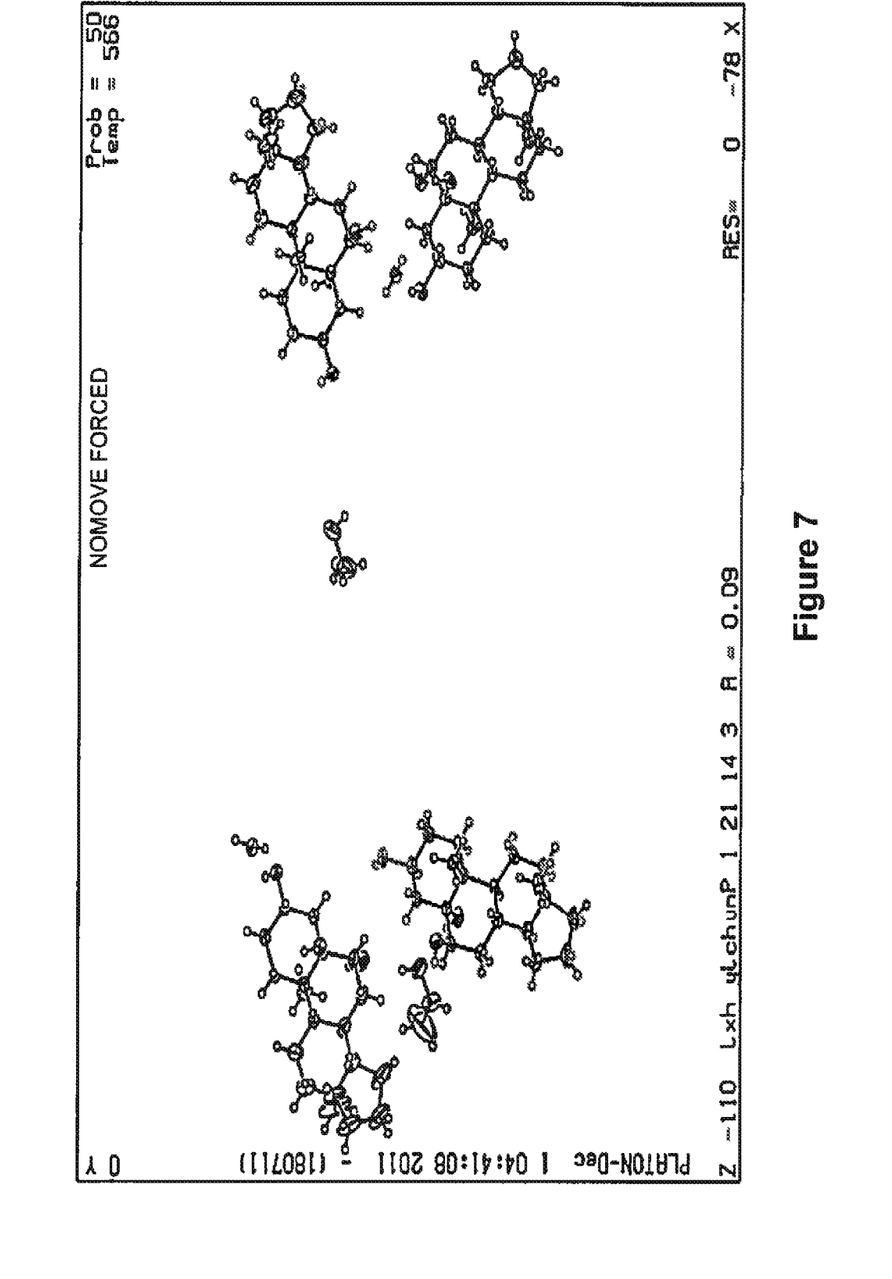
FIG. 7 shows the X-ray single crystal diffraction diagrams of crystalline form C of YC-6.

(3) The crystal structure information of crystalline form C of YC-6 obtained by X-ray single crystal diffraction is: the crystalline form belongs to the monoclinic crystal system and space group $P2_1$, with lattice parameters of a=17.14±0.08 Å, b=6.40±0.08 Å, c=34.89±0.08 Å, α=90.0°, β=91.05+0.5°, γ=90.0°, V=3827.48(9) Å³.

Figure 8:
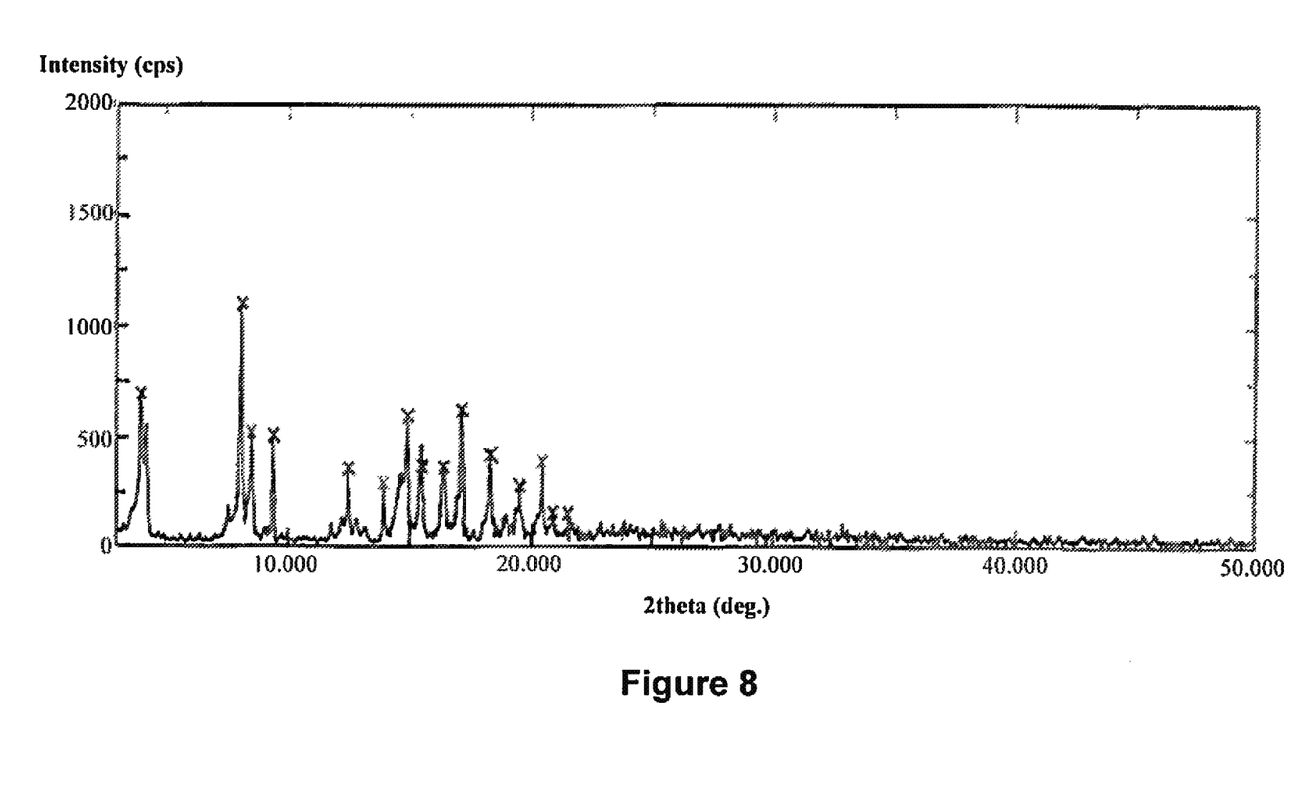
FIG. 8 shows the X-ray powder diffraction diagrams of crystalline form C of YC-6.

The crystalline form C of YC-6 showed diffraction peaks at diffraction angle 2θ values of 4.2±0.1, 8.5±0.1, 9.0±0.1, 12.5±0.1, 14.8±0.1, 15.4±0.1, 16.4±0.1, 16.8±0.2, 17.1±0.1, 18.3±0.1, 19.4±0.1, 20.8±0.1, 21.8±0.1, 24.1±0.1 degrees, with the X-ray powder diffraction diagrams showed in FIG. 8.

Figure 9:
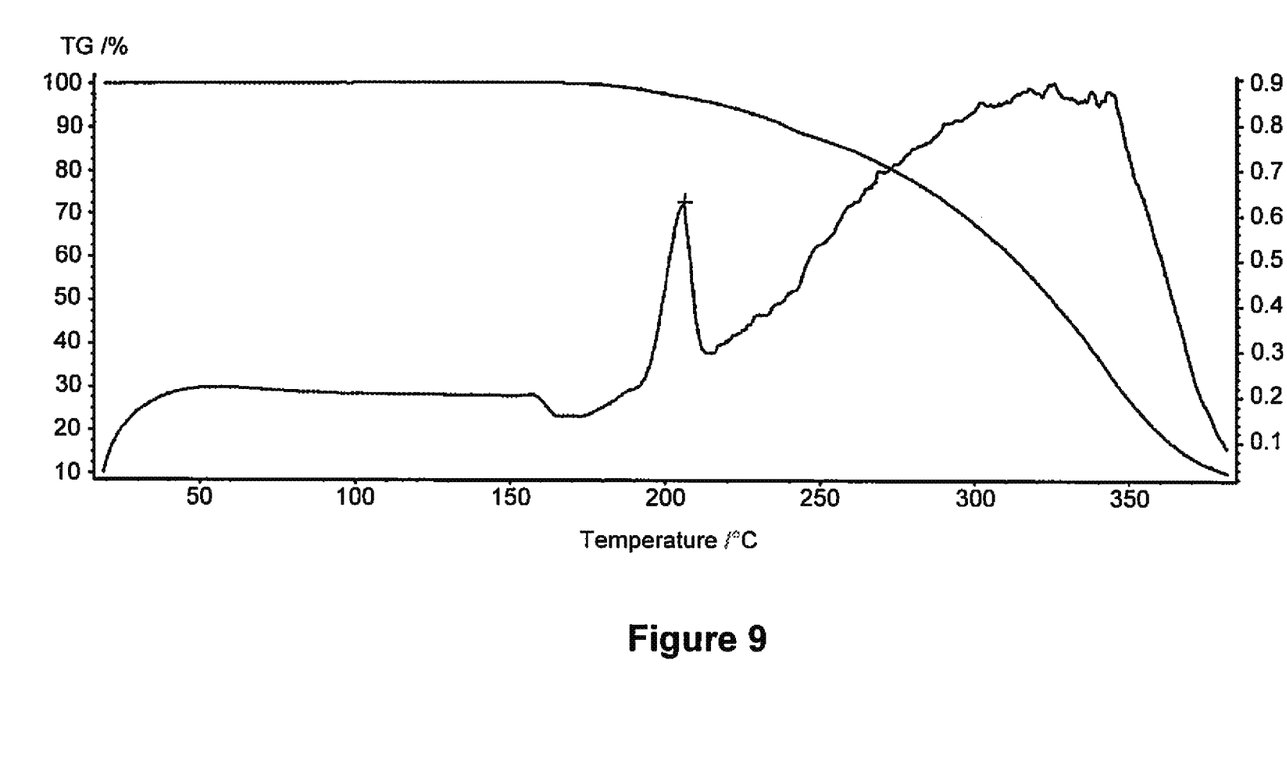
FIG. 9 shows the differential thermal analysis diagrams of crystalline form C of YC-6.

The differential scanning calorimetry (DSC) diagrams of crystalline form C of YC-6 is showed in FIG. 9, with the endothermic transition temperature of 206±2° C.

Figure 10:
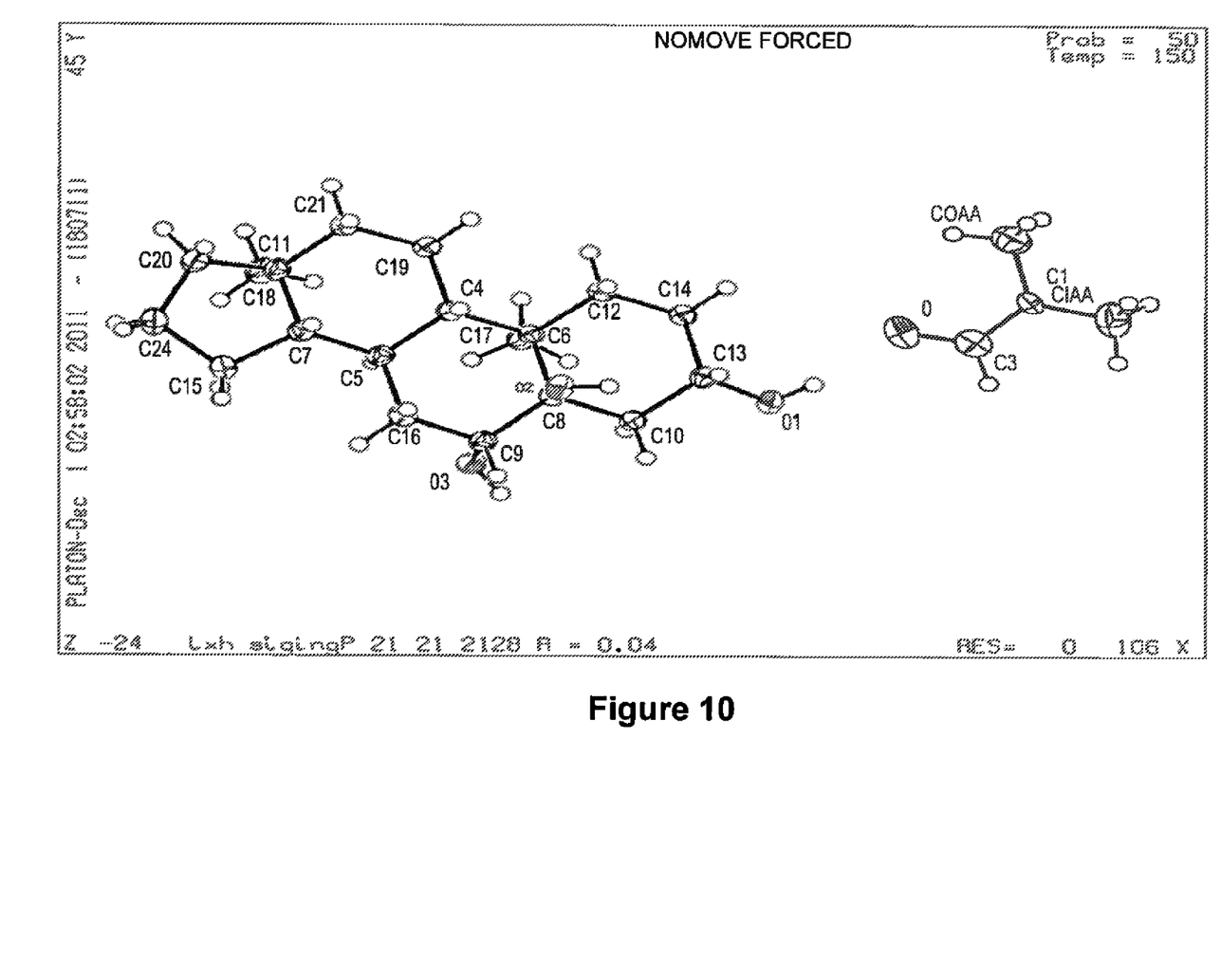
FIG. 10 shows the X-ray single crystal diffraction diagrams of crystalline form D of YC-6.

(4) The crystal structure information of crystalline form D of YC-6 obtained by X-ray single crystal diffraction is: the crystalline form belongs to the orthorhombic crystal system and space group $P2_12_12_1$, with lattice parameters of a=6.28±0.08 Å, b=12.56±0.08 Å, c=26.68±0.08 Å, α=90.0°, β=90.0°, γ=90.0°, V=2103.09(7) Å³.

Figure 11:
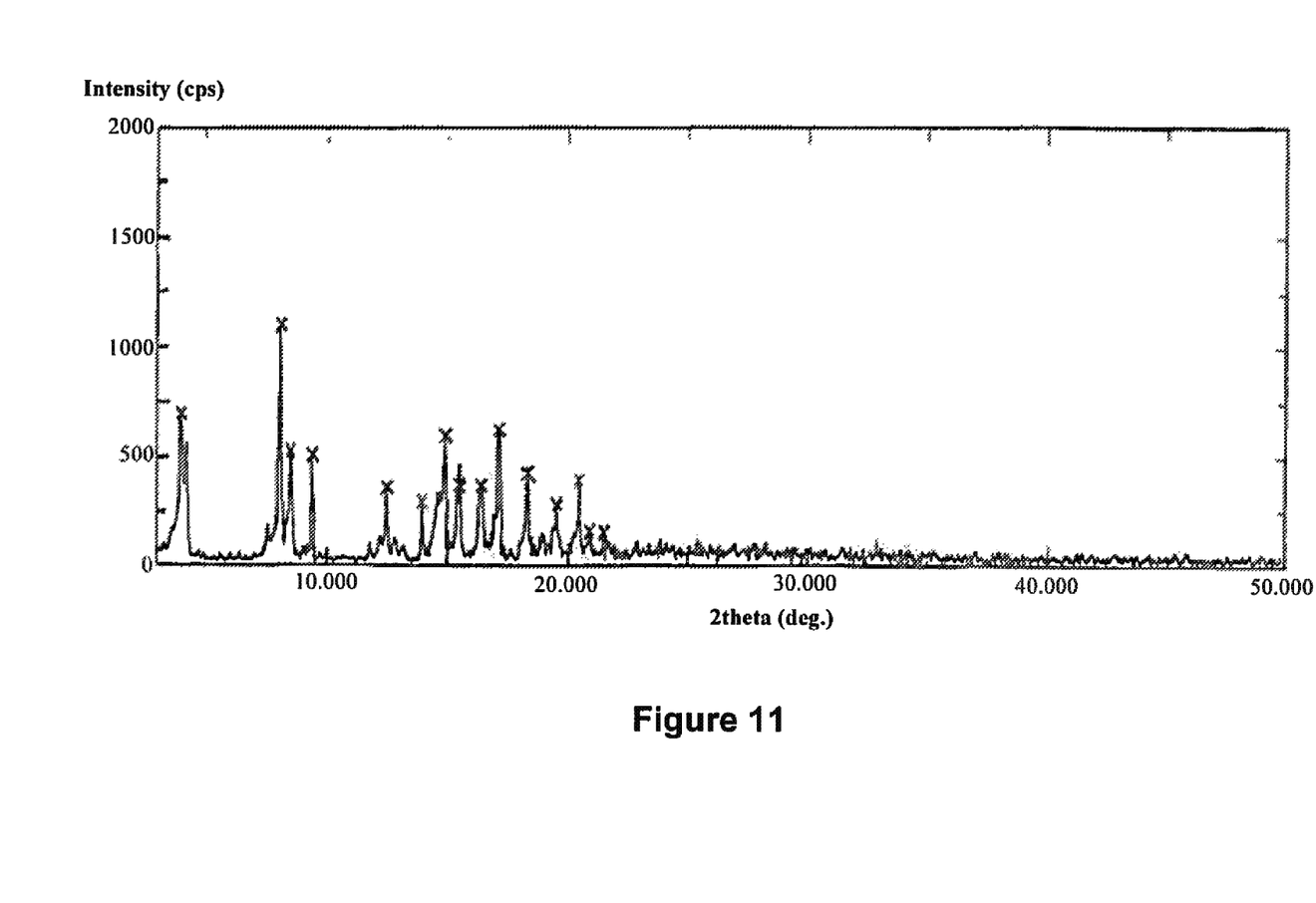
FIG. 11 shows the X-ray powder diffraction diagrams of crystalline form D of YC-6.

The crystalline form D of YC-6 showed diffraction peaks at diffraction angle 2θ values of 4.0±0.1, 8.1±0.1, 8.5±0.1, 9.4±0.1, 12.5±0.1, 14.0±0.1, 14.9±0.1, 15.5±0.1, 16.4±0.1, 17.1±0.1, 18.3±0.1, 19.5±0.1, 20.5±0.1, 20.9±0.1, 21.5-0.1 degrees, with the X-ray powder diffraction diagrams showed in FIG. 11.

Figure 12:
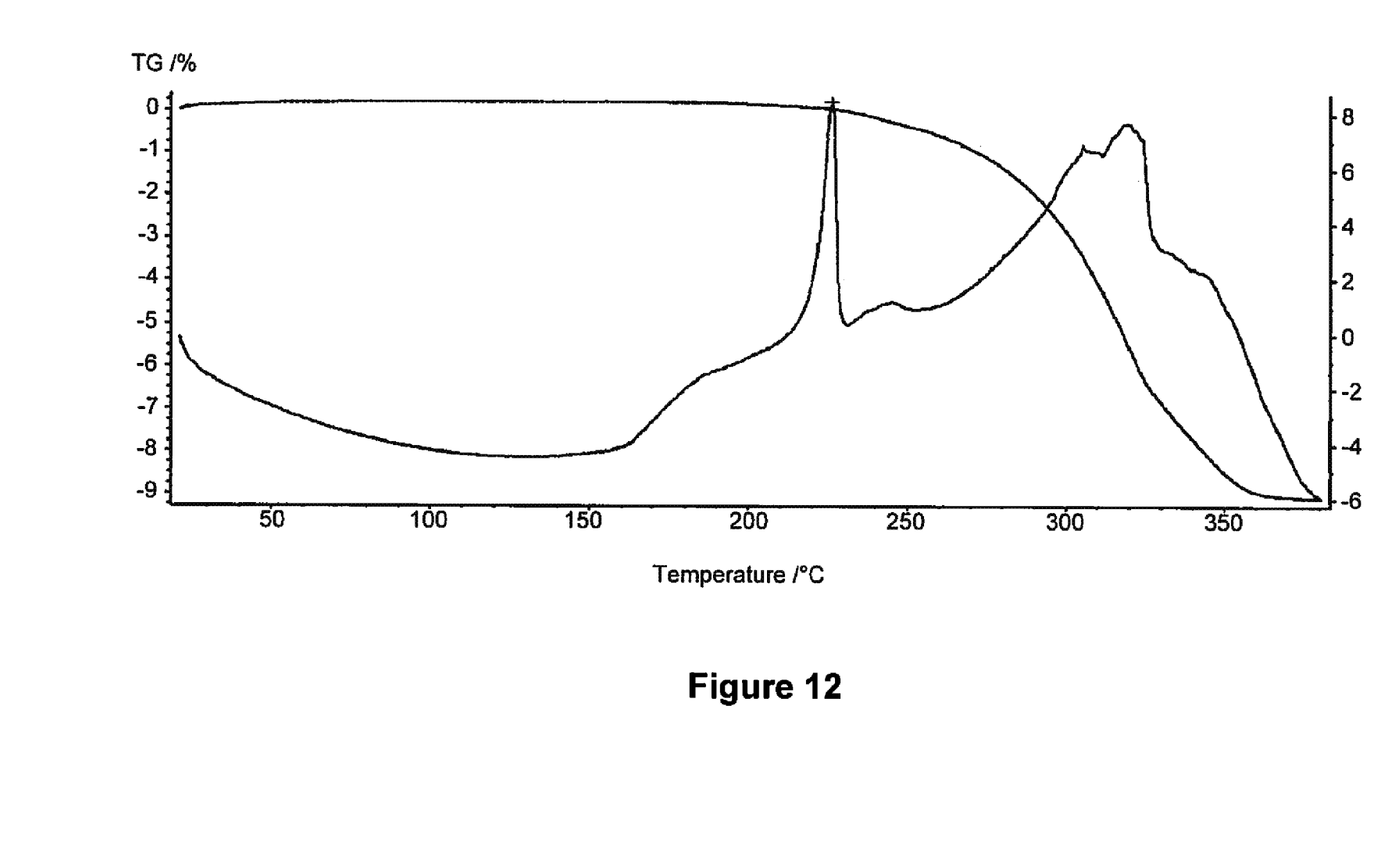
FIG. 12 shows the differential thermal analysis diagrams of crystalline form D of YC-6.

The differential scanning calorimetry (DSC) diagrams of crystalline form D of YC-6 is showed in FIG. 12, with the endothermic transition temperature of 226±2° C.

Example 1

Preparation of crystalline form A of YC-6: 0.5 g of YC-6 was dissolved in 8 mL of acetone (50-60° C.), which was added by the same amount of acetone to dilute, and then allowed to form a crystalline precipitate. The single crystal obtained thereby was directly subjected to X-ray single crystal diffraction. Then the crystal was filtrated by suction and was air-dried at 60° C. to a constant weight, which was subjected to X-ray powder diffraction and differential scanning calorimetry.

Example 2

Preparation of crystalline form A of YC-6: 0.5 g of YC-6 was dissolved in 10 mL of acetone at room temperature, which was added by the same amount of acetone to dilute, and then allowed to form a crystalline precipitate. The single crystal obtained thereby was directly subjected to X-ray single crystal diffraction. Then the crystal was filtrated by suction and was air-dried at 60° C. to a constant weight, which was subjected to X-ray powder diffraction and differential scanning calorimetry.

Example 3

Preparation of crystalline form A of YC-6: 0.5 g of YC-6 was dissolved in 7 mL of ethanol at room temperature, which was added by the same amount of ethanol to dilute, and then allowed to form a crystalline precipitate. The single crystal obtained thereby was directly subjected to X-ray single crystal diffraction. Then the crystal was filtrated by suction and was air-dried at 60° C. to a constant weight, which was subjected to X-ray powder diffraction and differential scanning calorimetry.

Example 4

Preparation of crystalline form A of YC-6: 0.5 g of YC-6 was dissolved in 12 mL of acetone at room temperature, which was added by water (a half amount of that of the acetone) to dilute, and then allowed to form a crystalline precipitate. The single crystal obtained thereby was directly subjected to X-ray single crystal diffraction. Then the crystal was filtrated by suction and was air-dried at 60° C. to a constant weight, which was subjected to X-ray powder diffraction and differential scanning calorimetry.

Example 5

Preparation of crystalline form A of YC-6: 0.5 g of YC-6 was dissolved in 10 mL of ethanol at room temperature, which was added by water (a half amount of that of the ethanol) to dilute, and then allowed to form a crystalline precipitate. The single crystal obtained thereby was directly subjected to X-ray single crystal diffraction. Then the crystal was filtrated by suction and was air-dried at 60° C. to a constant weight, which was subjected to X-ray powder diffraction and differential scanning calorimetry.

The tests showed that the crystals obtained in examples 1-5 share the same lattice parameters in X-ray single crystal diffraction, and that the crystals obtained thereby are all crystalline form A of YC-6.

Example 6

Preparation of crystalline form B of YC-6: 0.5 g of YC-6 was dissolved in 30 mL of ethyl acetate, which was then heated to 70-80° C. After that, the solution was added by 30 mL of ethyl acetate to dilute, and then cooled and allowed to form a crystalline precipitate. The single crystal obtained thereby was directly subjected to X-ray single crystal diffraction. Then the crystal was filtrated by suction and was air-dried at 70° C. to a constant weight, which was subjected to X-ray powder diffraction and differential scanning calorimetry.

Example 7

Preparation of crystalline form B of YC-6: 0.5 g of YC-6 was dissolved in 30 mL of ethyl acetate, which was then heated to 70-80° C. After that, the solution was added by 30 mL of hexamethylene to dilute, and then cooled and allowed to form a crystalline precipitate. The single crystal obtained thereby was directly subjected to X-ray single crystal diffraction. Then the crystal was filtrated by suction and was air-dried at 70° C. to a constant weight, which was subjected to X-ray powder diffraction and differential scanning calorimetry.

Example 8

Preparation of crystalline form B of YC-6: 0.5 g of YC-6 was dissolved in 8 mL of acetone, which was then heated to 50-60° C. After that, the solution was added by 24 mL of water to dilute, and then cooled and allowed to form a crystalline precipitate. The single crystal obtained thereby was directly subjected to X-ray single crystal diffraction. Then the crystal was filtrated by suction and was air-dried at 70° C. to a constant weight, which was subjected to X-ray powder diffraction and differential scanning calorimetry.

Example 9

Preparation of crystalline form B of YC-6: 0.5 g of YC-6 was dissolved in 12 mL of acetone, which was then heated to 50-60° C. After that, the solution was added by 36 mL of hexamethylene to dilute, and then cooled and allowed to form a crystalline precipitate. The single crystal obtained thereby was directly subjected to X-ray single crystal diffraction. Then the crystal was filtrated by suction and was air-dried at 70° C. to a constant weight, which was subjected to X-ray powder diffraction and differential scanning calorimetry.

The tests showed that the crystals obtained in examples 6-9 share the same lattice parameters in X-ray single crystal diffraction, and that the crystals obtained thereby are all crystalline form B of YC-6.

Example 10

Preparation of crystalline form C of YC-6: 0.5 g of YC-6 was dissolved in 12 mL of ethanol at room temperature, which was added by the same amount of ethanol to dilute, and then allowed to form a crystalline precipitate at 10° C. The single crystal obtained thereby was directly subjected to X-ray single crystal diffraction. Then the crystal was filtrated by suction and was air-dried at 70° C. to a constant weight, which was subjected to X-ray powder diffraction and differential scanning calorimetry.

Example 11

Preparation of crystalline form C of YC-6: 0.5 g of YC-6 was dissolved in 15 mL of ethanol at room temperature, which was added by the same amount of ethanol to dilute, and then allowed to form a crystalline precipitate at 10° C. The single crystal obtained thereby was directly subjected to X-ray single crystal diffraction. Then the crystal was filtrated by suction and was air-dried at 70° C. to a constant weight, which was subjected to X-ray powder diffraction and differential scanning calorimetry.

Example 12

Preparation of crystalline form C of YC-6: 0.5 g of YC-6 was dissolved in 15 mL of ethanol at room temperature, which was added by twice amount of ethanol to dilute, and then allowed to form a crystalline precipitate at 10° C. The single crystal obtained thereby was directly subjected to X-ray single crystal diffraction. Then the crystal was filtrated by suction and was air-dried at 70° C. to a constant weight, which was subjected to X-ray powder diffraction and differential scanning calorimetry.

The tests showed that the crystals obtained in examples 10-12 share the same lattice parameters in X-ray single crystal diffraction, and that the crystals obtained thereby are all crystalline form C of YC-6.

Example 13

Preparation of crystalline form D of YC-6: 0.5 g of YC-6 was dissolved in 10 mL of tetrahydrofuran at room temperature, which was added by the same amount of tetrahydrofuran to dilute, and then allowed to form a crystalline precipitate. The single crystal obtained thereby was directly subjected to X-ray single crystal diffraction. Then the crystal was filtrated by suction and was air-dried at 70° C. to a constant weight, which was subjected to X-ray powder diffraction and differential scanning calorimetry.

Example 14

Preparation of crystalline form D of YC-6: 0.5 g of YC-6 was dissolved in 10 mL of tetrahydrofuran at room temperature, which was added by twice amount of tetrahydrofuran to dilute, and then allowed to form a crystalline precipitate. The single crystal obtained thereby was directly subjected to X-ray single crystal diffraction. Then the crystal was filtrated by suction and was air-dried at 70° C. to a constant weight, which was subjected to X-ray powder diffraction and differential scanning calorimetry.

Example 15

Preparation of crystalline form D of YC-6: 0.5 g of YC-6 was dissolved in 15 mL of tetrahydrofuran at room temperature, which was added by the same amount of tetrahydrofuran to dilute, and then allowed to form a crystalline precipitate. The single crystal obtained thereby was directly subjected to X-ray single crystal diffraction. Then the crystal was filtrated by suction and was air-dried at 70° C. to a constant weight, which was subjected to X-ray powder diffraction and differential scanning calorimetry.

The tests showed that the crystals obtained in examples 13-15 share the same lattice parameters in X-ray single crystal diffraction, and that the crystals obtained thereby are all crystalline form D of YC-6.

The above examples are merely provided for description of the present invention, and are not intended to limit the scope of the present invention. The objects of the present invention can be achieved by skilled persons in the art in accordance with the disclosure of the present invention and the parameter ranges involved.

What is claimed is:

1. A crystalline form of 5α-androstane-3β,5,6β-triol, wherein the crystalline form is a transparent column-shaped crystal, and belongs to orthorhombic crystal system and space group $P2_12_12_1$, and wherein the crystalline form is characterized by lattice parameters of a=6.3±0.2 Å, b=12.6±0.2 Å, c=26.7±0.2 Å, α=90.0°, β=90°, γ=90.0°; and characterized by diffraction peaks at diffraction angle 2θ values of 4.0±0.2, 8.1±0.2, 8.5±0.2, 9.4±0.2, 12.5±0.2, 14.0±0.2, 14.9±0.2, 15.5±0.2, 16.4±0.2, 17.1±0.2, 18.3±0.2, 19.5±0.2, 20.5±0.2, 20.9±0.2, 21.5±0.2 degrees; and characterized by an endothermic transition temperature of 226±2° C.

2. A method for preparing the crystalline form of claim 1, comprising:
dissolving 5α-androstane-3β,5,6β-triol in tetrahydrofuran at room temperature, with a ratio of the 5α-androstane-3β,5,6β-triol to the tetrahydrofuran being 1 g:10-30 mL;
and
allowing to form a crystalline precipitate.

3. The method of claim 2, wherein the method comprises, after the dissolving, adding tetrahydrofuran to dilute.

4. The method of claim 3, wherein the dilution is performed at a ratio less than 5:1.

* * * * *